US00PP10544P

United States Patent [19]

Meilland

[11] Patent Number: Plant 10,544

[45] Date of Patent: Aug. 11, 1998

[54] GRANDIFLORA ROSE PLANT NAMED 'MEIHURGE'

[75] Inventor: Alain A. Meilland, Antibes, France

[73] Assignee: The Conard-Pyle Company, West Grove, Pa.

[21] Appl. No.: 796,581

[22] Filed: Feb. 6, 1997

[51] Int. Cl.[6] ..... A01H 5/00

[52] U.S. Cl. ..... Plt./17

[58] Field of Search ..... Plt./16, 17

*Primary Examiner*—Howard J. Lockeer

*Attorney, Agent, or Firm*—Burns, Doane, Swecker & Mathis, L.L.P.

[57] ABSTRACT

A new and distinct variety of grandiflora rose plant is provided which abundantly forms attractive brick red blossoms. The lant growth habit is semi-erect. The plant exhibits medium green and glossy foliage, as well as good disease resistance. The new variety is particularly well suited fro growing as attractive ornamentation in the landscape.

1 Drawing Sheet

SUMMARY OF THE INVENTION

The new variety of grandiflora rose plant was created by artificial pollination wherein two parents were crossed which previously had been studied in the hope that they would contribute the desired characteristics. The female parent (i.e., the seed parent) of the new variety was the product of the cross of the 'Tanorstar' variety (non-patented in the United States) and the 'Deltep' variety (non-patented in the United States). The male parent (i.e., the pollen parent) was the 'Meipraserpi' variety (non-patented in the United States). The parentage of the new variety can be summarized as follows:

('Tanorstar'×'Deltep')×'Meipraserpi'.

The seeds resulting from the above pollination were sown and small plants were obtained which were physically and biologically different from each other. Selective study resulted in the identification of a single plant of the new variety.

It was found that the new variety of grandiflora rose plant of the present invention possesses the following combination of characteristics:

(a) forms in abundance on a substantially continuous basis attractive brick red blossoms,
(b) exhibits a semi-erect growth habit,
(c) forms attractive dense dark green and glossy foliage,
(d) exhibits good disease resistance, and
(e) is particularly well suited for growing as attractive ornamentation in the landscape.

The new variety well meets the needs of the horticultural industry and is particularly well adapted for use as an attractive ornamental plant in an outdoors environment.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety initially was named 'urgence', and subsequently has been named the 'Meihurge' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during October while budded on *Rosa froebelii* understock and growing outdoors at Le Cannet des Maures, Var France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening:

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets — plan view — upper surface (left) and under surface (right); and FIG. 15 — illustrates specimens of leaves with five leaflets — plan view — upper surface (upper right) and under surface (lower left).

DETAILED DESCRIPTION

Figures 1, 2, 3, 4, 5, 6, 7, 8, 9, 10, 11, 14, 15, 18:
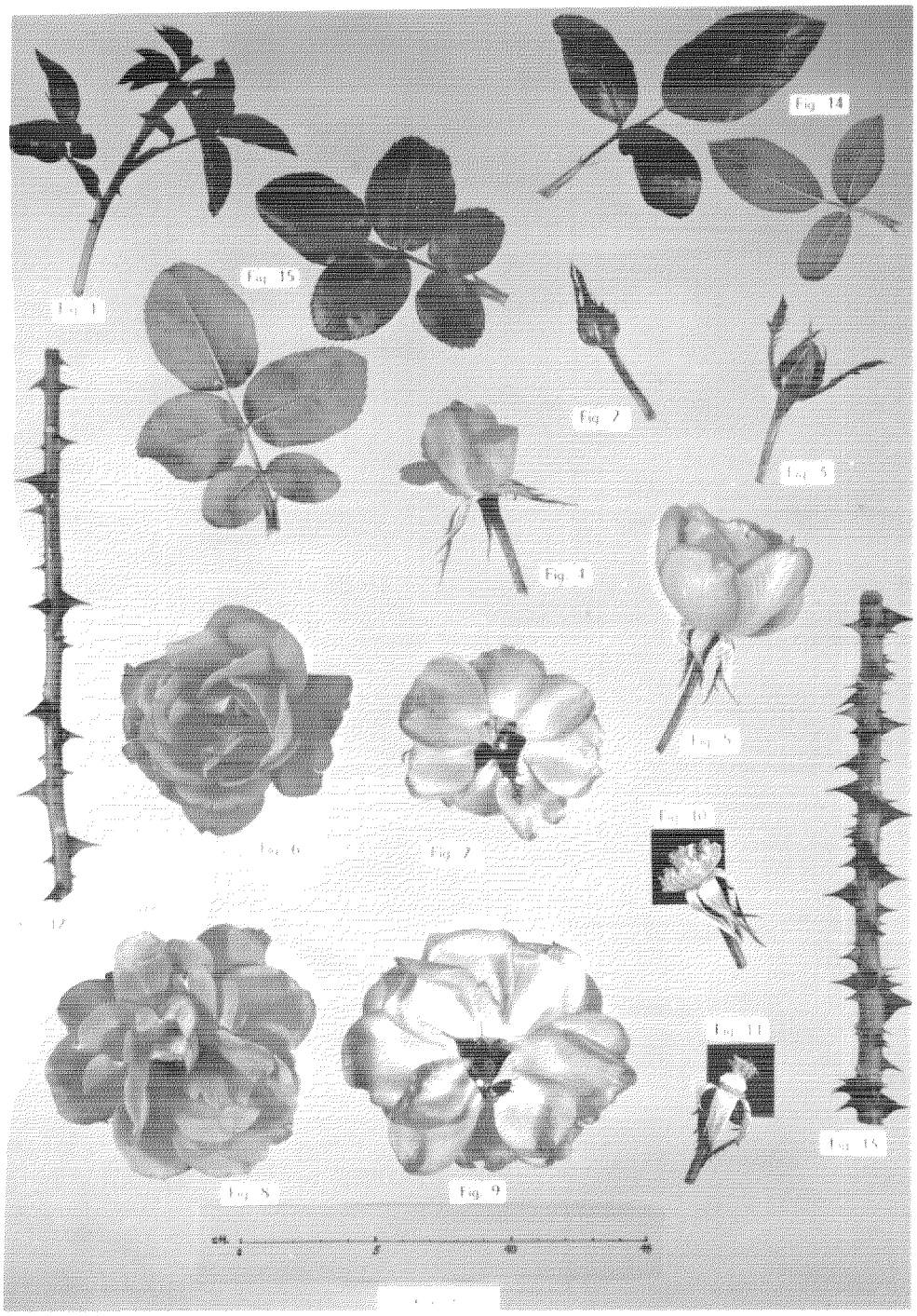

The chart used in the identification of the colors is that of The Royal Horticultural Society (R.H.S. Colour Chart). The description is based on the observation of three year-old plants during June while budded on *Rosa froebelii* understock and growing outdoors at Le Cannet des Maures, Var, France. The coloration in common terms precedes reference to the chart in some instances.

Class: Grandiflora.

Plant:

*Height.*—Approximately 90 cm. on average at the end of two growing seasons.

*Habit.*—Compact and semi-erect.

Branches:

*Color.*—Young Stems: Yellow-Green Group 146C. Adult wood: Yellow-Green Group 146B.

*Thorns.*—Size: vary from small to large. Quantity: numerous, and more than typical for the class (as illustrated). Color: reddish (Red Group 53B) on young stems and Havana brown (Greyed-Orange Group 175B) on adult wood.

Leaves:

*Stipules.*—Narrow, adnate, and pectinate.

*Petioles.*—Upper surface: striped reddish-brown on young foliage, and medium green on adult foliage. On the adult foliage are near Green Group 137D with highlights of Yellow-Green Group 144C. Under surface: light green, and bear small thorns.

*Leaflets.*—Number: 3, 5 (most often), and 7. Shape: oval. Size: medium for class. Serration: simple and regular (as illustrated). Texture: consistent. General appearance: very dense, medium green, and glossy. Color (young foliage): upper surface: Green Group 139A and widely suffused with reddish brown. under surface: Green Group 139A and widely suffused with reddish brown. Color (adult foliage): upper surface: near Green Group 139A. under surface: near Greyed-Green Group 191A.

Inflorescence:

*Number of flowers.*—Usually two to five per stem.

*Peduncle.*—very strong without bent necks, light green (Green Group 138B) suffused with reddish coloration (Red Group 53C) bears small relatively soft thorns and acicules, and the length is approximately 3.5 cm. on average.

*Stem length.*—Commonly approximately 30 to 38 cm. on average.

*Sepals.*—Upper surface: tomentose, and greenish (Greyed-Green Group 194D) in coloration. Under surface: light green (commonly between Green Groups 143A and 143B) in coloration and with a few extensions. The extensions are short and near fanlike in appearance.

*Buds.*—Shape: conical. Length: approximately 2.5 cm. on average. Size: medium. Color upon opening: upper surface: near Greyed-Orange Group 169A. under surface: near Greyed-Orange Group 169A.

*Flower.*—Shape: Cup-shaped and globase. Diameter: approximately 9 to 10 cm. on average. Color (when opening begins): upper surface: near Brick Red, Orange-Red Group 35A. under surface: near Brick Red, Orange-Red Group 35A and lightly suffused with Orange-Red Group 35B. Color (when blooming): upper surface: Near Brick Red, Orange-Red Group 35A. under surface: near Brick Red, Orange-Red Group 35C. Color (at end of opening): upper surface: near Brick Red, Orange-Red Group 35A. under surface: near light Brick Red, Orange-Red Group 35D. Fragrance: absent. Petal number: approximately 33 on average. Petal shape: orbicular, and the base is obtuse and the tips are rounded. Petal texture: consistent. Stamen number: approximately 130 on average. Anthers: ochre in coloration. Filaments: yellowish in coloration. Pistils: approximately 75 on average. Stigmas: yellowish in coloration. Styles: yellowish in coloration. Receptacle: light green, smooth, and in longitudinal section in the shape of a funnel. Tendency to form hips: none. Life of blossoms: commonly approximately 7 to 10 days on the plant and approximately 3 to 5 days when cut and placed in a vase.

Development

*Vegetation.*—Strong.

*Blooming.*—Abundant, precocious, and substantially continuous.

*Resistance to diseases.*—Good with respect to Powdery Mildew, Blackspot, and Downy Mildew.

*Resistance to frost.*—Good.

I claim:

1. A new and distinct variety of grandiflora rose plant characterized by the following combination of characteristics:

(a) forms in abundance on a substnatially continuous basis attractive Brick Red blossoms,
(b) exhibits a semi-erect growth habit,
(c) forms attractive dense dark green and glossy foliage,
(d) exhibits good disease resistance, and
(e) is particularly well suited for growing as attractive ornamentation in the landscape;

substantially as herein shown and described.

* * * * *